(12) United States Patent
Choong et al.

(10) Patent No.: US 8,998,913 B2
(45) Date of Patent: Apr. 7, 2015

(54) PATELLA RESECTION ASSEMBLY

(75) Inventors: Peter F. M. Choong, East Melbourne (AU); Raymond E. Randle, Mudgeeraba (AU); Abraham P. Wright, Winona Lake, IN (US)

(73) Assignee: Depuy (Ireland), Cork (IE)

( * ) Notice: Subject to any disclaimer, the term of this patent is extended or adjusted under 35 U.S.C. 154(b) by 413 days.

(21) Appl. No.: 13/548,676

(22) Filed: Jul. 13, 2012

(65) Prior Publication Data

US 2013/0184712 A1  Jul. 18, 2013

Related U.S. Application Data

(60) Provisional application No. 61/540,061, filed on Sep. 28, 2011.

(51) Int. Cl.
| | | |
|---|---|---|
| *A61B 17/58* | (2006.01) | |
| *A61B 17/60* | (2006.01) | |
| *A61F 2/00* | (2006.01) | |
| *A61B 17/17* | (2006.01) | |
| *A61B 17/15* | (2006.01) | |

(52) U.S. Cl.
CPC ........... *A61B 17/1767* (2013.01); *A61B 17/158* (2013.01)

(58) Field of Classification Search
CPC ............. A61B 17/1677; A61B 17/158; A61B 17/1767; A61B 17/8866; A61B 17/1764; A61B 2019/304
See application file for complete search history.

(56) References Cited

U.S. PATENT DOCUMENTS

| | | |
|---|---|---|
| 2,181,746 A | 11/1939 | Siebrandt |
| 3,835,849 A | 9/1974 | McGuire |
| D260,927 S | 9/1981 | Glenn |
| D281,622 S | 12/1985 | Diamond |
| 4,565,192 A | 1/1986 | Shapiro |
| 4,633,862 A | 1/1987 | Petersen |
| 5,002,547 A | 3/1991 | Poggie et al. |
| 5,021,055 A | 6/1991 | Burkinshaw |

(Continued)

FOREIGN PATENT DOCUMENTS

| | | |
|---|---|---|
| EP | 992222 A3 | 4/2000 |
| EP | 2574314 A1 | 4/2013 |

(Continued)

OTHER PUBLICATIONS

DePuy International Ltd., PFC Sigma Rotating Platform Knee System with MBT Tray, Surgical Technique Brochure, 2003, (43 pages), Cat. No. 9068-96-000, DePuy International Ltd., Leeds, England.

(Continued)

*Primary Examiner* — David Bates
*Assistant Examiner* — Samuel Hanna (57) ABSTRACT

A patella resection assembly comprises a handle, slide member and two claw members. The slide member is movably mounted on the handle and includes two diverging arms. Inner edges of the diverging arms contact outer edges of the claw members so that distal movement of the slide member causes the claw members to move toward each other and close around a patella. The claw members and slide member have teeth for grasping the patella as the claw members move together. The claw members also have flat co-planar surfaces for guiding the path of a saw blade during resection of the patella.

5 Claims, 6 Drawing Sheets

(56) References Cited

U.S. PATENT DOCUMENTS

| | | |
|---|---|---|
| 5,108,401 A | 4/1992 | Insall et al. |
| 5,116,338 A | 5/1992 | Poggie |
| 5,129,907 A | 7/1992 | Heldreth |
| 5,129,908 A | 7/1992 | Petersen |
| 5,147,365 A | 9/1992 | Whitlock et al. |
| 5,222,955 A | 6/1993 | Mikhail |
| 5,250,050 A | 10/1993 | Poggie et al. |
| 5,284,482 A | 2/1994 | Mikhail |
| 5,284,485 A | 2/1994 | Kammerer et al. |
| 5,382,254 A | 1/1995 | McGarry et al. |
| 5,415,663 A | 5/1995 | Luckman et al. |
| 5,470,328 A | 11/1995 | Furnish et al. |
| 5,484,451 A | 1/1996 | Akopov et al. |
| D367,531 S | 2/1996 | Price et al. |
| 5,520,692 A | 5/1996 | Ferrante |
| 5,536,271 A | 7/1996 | Daly |
| 5,542,947 A | 8/1996 | Treacy |
| D373,635 S | 9/1996 | Price et al. |
| 5,575,793 A | 11/1996 | Carls et al. |
| 5,582,615 A | 12/1996 | Foshee et al. |
| 5,593,450 A | 1/1997 | Scott et al. |
| 5,611,802 A | 3/1997 | Samuelson et al. |
| 5,626,607 A | 5/1997 | Malecki et al. |
| 5,667,512 A | 9/1997 | Johnson |
| 5,716,362 A | 2/1998 | Treacy |
| 5,827,279 A | 10/1998 | Hughett et al. |
| 5,941,884 A | 8/1999 | Corvelli et al. |
| 5,944,723 A | 8/1999 | Colleran |
| 5,968,051 A | 10/1999 | Luckman et al. |
| 6,010,509 A | 1/2000 | Delgado et al. |
| 6,056,754 A | 5/2000 | Haines et al. |
| 6,074,343 A * | 6/2000 | Nathanson et al. ........... 600/214 |
| 6,074,425 A | 6/2000 | Pappas |
| 6,190,391 B1 | 2/2001 | Stubbs |
| 6,205,884 B1 | 3/2001 | Foley et al. |
| D459,474 S | 6/2002 | Bratt et al. |
| 6,419,675 B1 | 7/2002 | Gallo, Sr. |
| D463,550 S | 9/2002 | Sherman |
| 6,551,316 B1 | 4/2003 | Rinner |
| 6,855,150 B1 | 2/2005 | Linehan |
| 6,866,667 B2 | 3/2005 | Wood et al. |
| D549,331 S | 8/2007 | Tomatsu et al. |
| 7,344,540 B2 | 3/2008 | Smucker et al. |
| 7,566,335 B1 | 7/2009 | Scott et al. |
| 7,632,279 B2 | 12/2009 | Bastian |
| 7,780,594 B2 | 8/2010 | Hutton |
| 7,806,899 B2 | 10/2010 | Hogg et al. |
| 7,878,989 B2 | 2/2011 | McMinn |
| 7,891,071 B2 | 2/2011 | Collazo |
| D634,011 S | 3/2011 | Phillips et al. |
| D638,541 S | 5/2011 | Claypool |
| 7,972,383 B2 | 7/2011 | Goldstein et al. |
| D642,678 S | 8/2011 | Dockstader et al. |
| D646,389 S | 10/2011 | Claypool et al. |
| 8,216,242 B2 | 7/2012 | Marchyn |
| 2002/0115987 A1 | 8/2002 | Hildwein et al. |
| 2004/0153066 A1 | 8/2004 | Coon |
| 2004/0162561 A1 | 8/2004 | Marchyn et al. |
| 2005/0240196 A1 | 10/2005 | Davis et al. |
| 2006/0142777 A1 | 6/2006 | Bastian |
| 2007/0038216 A1 * | 2/2007 | Hamada ........................ 606/53 |
| 2007/0118141 A1 | 5/2007 | Marchyn et al. |
| 2007/0162031 A1 | 7/2007 | Hogg |
| 2007/0233142 A1 | 10/2007 | Oliver |
| 2007/0260227 A1 | 11/2007 | Phan |
| 2008/0097450 A1 | 4/2008 | Brown et al. |
| 2008/0114366 A1 | 5/2008 | Smucker et al. |
| 2008/0177394 A1 | 7/2008 | Chauhan |
| 2008/0228190 A1 | 9/2008 | Sherry et al. |
| 2008/0306484 A1 | 12/2008 | Coon |
| 2009/0264737 A1 | 10/2009 | Haechler et al. |
| 2009/0326661 A1 | 12/2009 | Wright et al. |
| 2010/0030223 A1 | 2/2010 | Kellar |
| 2010/0152742 A1 | 6/2010 | Nevelös et al. |
| 2010/0168753 A1 | 7/2010 | Edwards et al. |
| 2011/0066193 A1 | 3/2011 | Lang |
| 2012/0078261 A1 | 3/2012 | Kecman et al. |
| 2013/0023883 A1 | 1/2013 | Wright |
| 2013/0023890 A1 | 1/2013 | Kecman |
| 2013/0030443 A1 | 1/2013 | Wright |
| 2013/0030539 A1 | 1/2013 | Wright |
| 2013/0035693 A1 | 2/2013 | Wright |
| 2013/0079788 A1 | 3/2013 | Spencer Jones |
| 2013/0079789 A1 | 3/2013 | Randle |
| 2013/0211410 A1 | 8/2013 | Landes |

FOREIGN PATENT DOCUMENTS

| | | |
|---|---|---|
| WO | WO 9945856 A1 | 9/1999 |
| WO | WO 2008112996 A1 | 9/2008 |

OTHER PUBLICATIONS

DePuy Orthopaedics, Inc., LCS High Performance Instruments, Surgical Technique Guide, 2008, (44 pages), Pub. No. 0612-85-506, DePuy Orthopaedics, Inc., Warsaw, IN.

DePuy Orthopaedics, Inc., Sigma High Performance Instruments, Classic Surgical Technique, 2010, (52 pages), Pub. No. 0612-89-510, DePuy Orthopaedics, Inc., Warsaw, IN.

DePuy Orthopaedics, Inc., Sigma High Performance Instruments, Design Rationale, 2009, (12 pages), Pub. No. 0612-54-506 (Rev.2), DePuy Orthopaedics, Inc., Warsaw, IN.

European Search Report, European Patent Application No. 11175824.9-2310, Dec. 16, 2011, (8 pages).

European Search Report, European Patent Application No. 11175824.9-2310, Mar. 1, 2013 (7 pages).

* cited by examiner

PATELLA RESECTION ASSEMBLY

CROSS-REFERENCE TO RELATED APPLICATION

This application claims priority to U.S. Prov. App. No. 61/540,061 filed Sep. 28, 2011, entitled "Patella Resection Assembly," which is incorporated by reference herein in its entirety.

TECHNICAL FIELD

The present disclosure relates generally to orthopaedic surgical instruments and more particularly to patella resectioning guides.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. In some cases, the knee prosthesis may also include a prosthetic patella component, which is secured to a posterior side of the patient's surgically-prepared patella. To prepare the patella, an orthopaedic surgeon first resects the posterior dome side of the patient's natural patella to secure the prosthetic component thereto. In use, the patella component articulates with the patient's natural or prosthetic femur during extension and flexion of the patient's knee.

To facilitate the replacement of the natural joint with the knee prosthesis, orthopaedic surgeons use a variety of orthopaedic surgical instruments such as, for example, cutting blocks, drill guides, milling guides, and other surgical instruments. Typically, the orthopaedic surgical instruments are generic with respect to the patient such that the same orthopaedic surgical instrument may be used on a number of different patients during similar orthopaedic surgical procedures.

In resecting the patella, surgeons frequently perform the resection free-hand. However, free-hand cutting the patella is not as accurate as a guided resection. Moreover, it is important that a sufficient amount of bone stock remain after resection to accept the fixation means for the patellar prosthesis and to maintain the integrity of the remaining patella. To ensure that the patella implant is properly positioned and that an appropriate amount of bone remains after resection, a resection guide is needed.

Depending on a number of factors, including the size of the patient, native patellae are of substantially different sizes. Accordingly, if a resection guide is to be used, either the guide must be provided in a plurality of sizes to accommodate variations in patellae size or an adjustable resection guide must be used.

SUMMARY

The present invention provides an adjustable patella resection guide that assists the surgeon in performing a resection while the patella is gripped securely.

In illustrative embodiments, the present invention provides a patella resection assembly comprising a handle, a slide member and first and second claw members. The handle has a proximal end, a distal end, and a longitudinal axis between the proximal end and distal end defining a longitudinal plane. The slide member is movably mounted on the handle and includes a first bone-gripping member, a base, a first arm and a second arm. The first arm and the second arm extend from the base in a distal direction to free distal ends. The first arm is positioned on one side of the longitudinal plane and the second arm is positioned on the opposite side of the longitudinal plane. The first arm has an inner edge facing the longitudinal plane and the second arm has an inner edge facing the longitudinal plane; the inner edges diverge in the distal direction. The slide member is selectively movable in a linear direction along the longitudinal axis of the handle toward and away from the proximal end and distal end of the handle between a first position and a second position. The second position is more distal than the first position. The first claw member extends from the distal end of the handle to a free end. The first claw member is positioned on one side of the longitudinal plane, and has a flat and planar surface for guiding a saw blade, a second bone-gripping member at the first free end, a curved outer edge and a second end mounted to the handle. The second claw member extends from the distal end of the handle to a free end. The second claw member is positioned on the side of the longitudinal plane opposite the position of the first claw member, and has a flat and planar surface co-planar with the flat and planar surface of the first claw member, a third gripping member at the free end, a curved outer edge and a second end mounted to the handle. The free end of the first claw member and the free end of the second claw member are spaced distally from the distal end of the handle. The first bone-gripping member, first claw member and the second claw member define an opening between them to receive a patella. The inner edge of the first arm of the slide member and the outer edge of the first claw member contact each other, and the inner edge of the second arm of the slide member and the outer edge of the second claw member contact each other. Longitudinal movement of the slide member from the first position to the second position causes the first bone-gripping member to move distally and the free ends of the first claw member and the second claw member to move toward each other. The opening defined by the first bone-gripping member, first claw member and the second claw member has one size when the slide member is in the first position and a smaller size when the slide member is in the second position.

In a more particular embodiment, a fourth gripping member extends from the first claw member toward the opening at a position spaced from the free end of the first claw member and a fifth gripping member extends from the second claw member toward the opening at a position spaced from the free end of the second claw member.

In another more particular embodiment, the first and second claw members are pivotally connected to the handle and longitudinal movement of the slide member from the first position to the second position causes the first claw member and the second claw member to pivot.

In another alternative embodiment, the first and second claw members are connected to the handle by linear movement connectors so that longitudinal movement of the slide member from the first position to the second position causes the first claw member and the second claw member to move linearly toward each other.

In another more particular embodiment, the slide member includes a middle arm extending from the base along the longitudinal axis of the handle to a distal end and the first bone-gripping member is at the distal end of the middle arm.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

References to "proximal" and "distal" in reference to the illustrated patella resection assemblies are in relation to the user of the instruments. Thus, proximal refers to a location nearer to the user and distal refers to a location further from the user.

Figure 1:
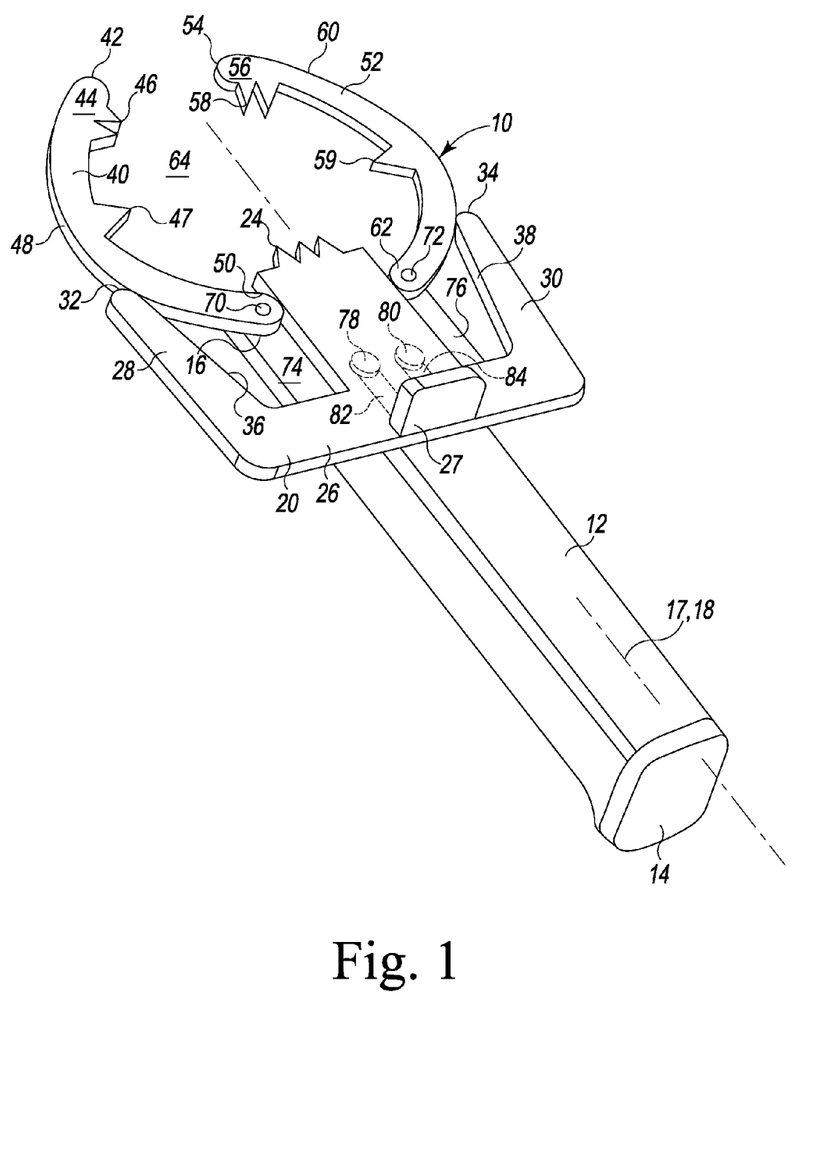
FIG. 1 is a perspective view of one embodiment of a patella resection assembly incorporating the principles of the present invention.

Referring to FIG. 1, a first embodiment of a patella resection assembly 10 is illustrated. The illustrated patella resection assembly 10 comprises a handle 12, a slide member 20 and two claw members 40, 52.

The handle 12 has a proximal end 14, a distal end 16, and a longitudinal axis 18. The longitudinal axis 18 lays in a longitudinal plane 17 dividing the assembly 10 into medial and lateral halves.

The slide member 20 includes a first bone-gripping member 24, a base 26, a first outer arm 28 and a second outer arm 30. The first arm 28 extends distally from the base 26 to a free distal end 32 and the second arm 30 extends distally from the base 26 to a free distal end 34. The slide member 20 also includes a middle arm 35 extending distally from the base 26 along the longitudinal plane 17. The first illustrated slide member 20 also includes a tab 27 extending upwardly from the base 26.

Figure 2:
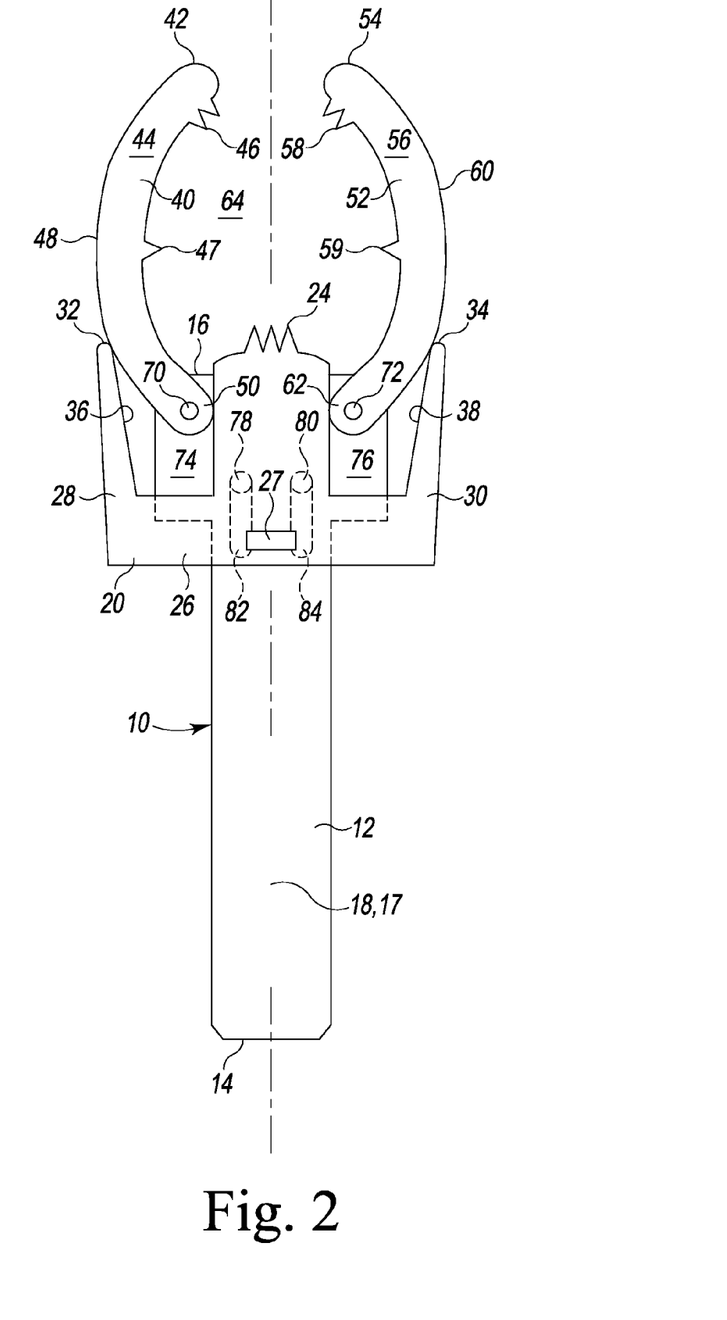
FIG. 2 is a top plan view of the patella resection assembly of FIG. 1, illustrating the assembly in a first, open position.
Figure 3:
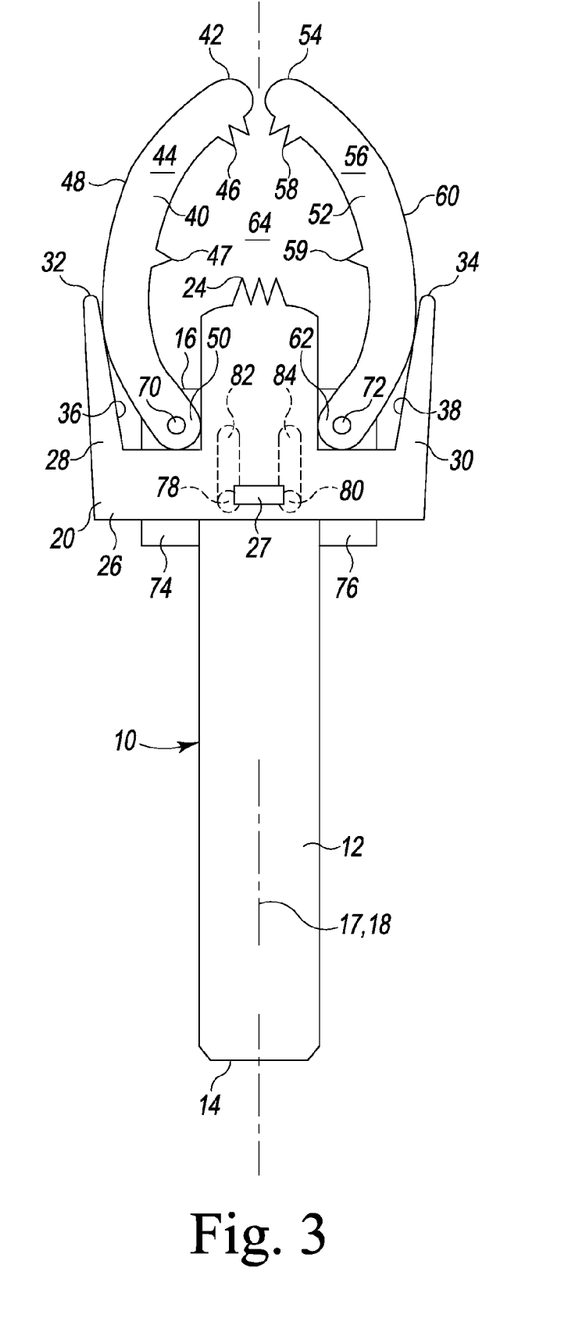
FIG. 3 is a top plan view of the patella resection assembly of FIGS. 1-2, illustrating the assembly in a second, closed position.

The slide member 20 is selectively movable with respect to the handle 12 in a linear direction along the longitudinal axis 18 of the handle between a first position shown in FIG. 2 and a second position shown in FIG. 3. In the second position of FIG. 3, the slide 20 is more distal than in the first position of FIG. 1.

The first claw member 40 extends from the distal end 16 of the handle 12 along one side of the longitudinal plane 17 to a first free distal end 42. The first claw member 40 has a flat and planar surface 44 for guiding a saw blade (not shown), a second bone-gripping member 46 at the first free end 42, a curved outer edge 48 and a second end 50 mounted to the handle 12.

The second claw member 52 extends from the distal end 16 of the handle 12 along the side of the longitudinal plane 17 opposite from the first claw member 40 to a second free distal end 54. The second claw member 52 has a flat and planar surface 56 co-planar with the flat and planar surface 44 of the first claw member 40, a third bone-gripping member 58 at the second free distal end 54, a curved outer edge 60 and a second end 62 mounted to the handle 12.

As illustrated in FIGS. 1-3, the first free end 42 of the first claw member 40 and the second free end 54 of the second claw member 52 are spaced distally from the distal end 16 of the handle 12. The first claw member 40, second claw member 52 and first bone-gripping member 24 define an opening 64 between them to receive a patella. The illustrated embodiment also includes fourth and fifth bone-gripping members 47, 59 extending into the opening 64 from the inner edges of the claw members 40, 52 along the most medial and most lateral portions of the inner edges.

All of the bone-gripping members 24, 46, 47, 58, 59 in the illustrated embodiment comprise one or more pointed or sharp teeth facing into the opening 64. All of the teeth of the bone-gripping members 24, 46, 47, 58, 59 lie in a plane that is perpendicular to the longitudinal plane 17. The teeth are positioned and oriented so that when the patella is received between and engaged by the teeth, a plurality of points on the patella are engaged (such as three spaced points) so that the patella is held with no relative movement between the patella and the patella resection guide. All of the bone-gripping members 24, 46, 47, 58, 59 may be formed integrally with their respective parts or formed as separate elements fixed to their respective parts.

In the assembly 10, the inner edges 36, 38 of the side arms 28, 30 of the slide member 20 contact the curved outer edges 48, 60 of the claw members 40, 52 when the slide member 20 is in the first position of FIG. 2 and when the slide member 20 is in the second position of FIG. 3. As can be seen from FIGS. 1-3, the curved outer edges 48, 60 of the claw members 40, 52 are substantially elliptical in shape, curving outwardly from their second ends 50, 62 to their widest points and then curving back inwardly toward the distal ends 42, 54. The inner edges of the claw members are similarly shaped.

As shown in FIGS. 1-3, the inner edges 36, 38 of the side arms 28, 30 are substantially straight, and diverge outwardly from the base 26 in the distal direction. Thus, the space between the inner edges 36, 38 is greatest at the free distal ends 32, 34 and least at the junctions of the side arms 28, 30 with the base 26. As can be seen in FIGS. 2 and 3, as the slide member 20 is moved distally from the position shown in FIG. 2 to the position shown in FIG. 3, the contacts between the diverging inner edges 36, 38 of the side arms 28, 30 and curved outer edges 48, 60 of the claw members 40, 52 change, so that the contacts are at more proximal portions of the inner edges 36, 38 of the side arms 28, 30 where the space between the inner edges 36, 38 is more narrow. Thus, distal movement of the slide member 20 forces the claw members 40, 52 to move towards each other and causes the gap between all of the bone-gripping members 24, 46, 58 to decrease until the bone-gripping members contact the periphery of a patella positioned in the opening 64.

To allow for such movement of the claw members 40, 52, the first illustrated embodiment uses a pivotal connection between the claw members 40, 52 and the handle 12. This pivotal connection may comprise pins, such as those shown at 70, 72 in FIGS. 1-3 received in cylindrical holes. In the illustrated embodiment, the pins 70, 72 extend upward from shoulders 74, 76 extending outwardly from the distal end 16 of the handle 12 and the cylindrical holes are formed in the proximal ends 50, 62 of the claw members 40, 52. It should be understood that this pin and hole arrangement is provided as an example of a possible pivot connection that may be used with the first embodiment; other types of pivot connections that allow the claw members to pivot could be employed and the invention is not limited to the illustrated pivot connection mechanism unless expressly called for in the claims.

Figure 4:
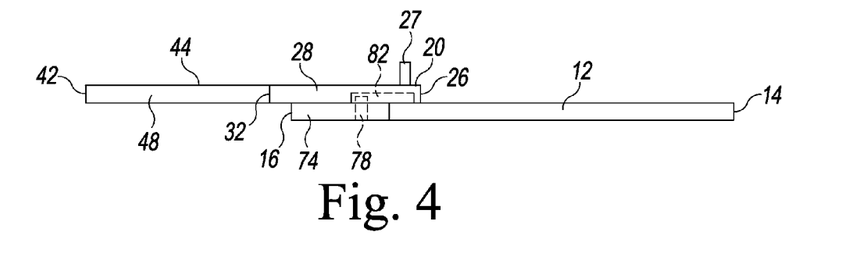
FIG. 4 is a side elevation of the patella resection assembly of FIGS. 1-3 in the first, open position.
Figure 5:
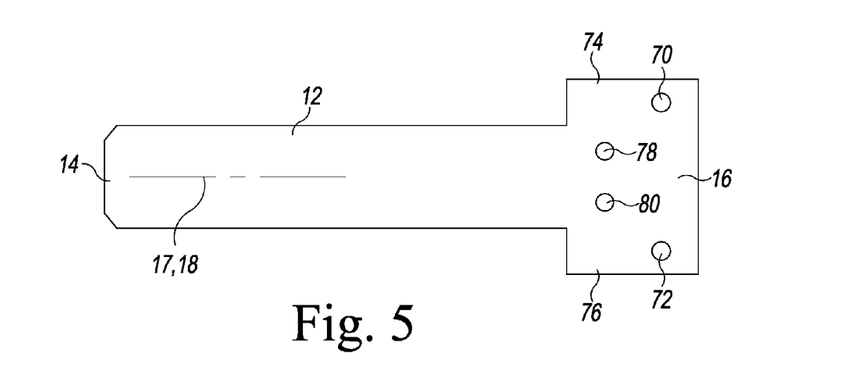
FIG. 5 is a top plan view of the handle of the patella resection assembly of FIGS. 1-4.
Figure 6:
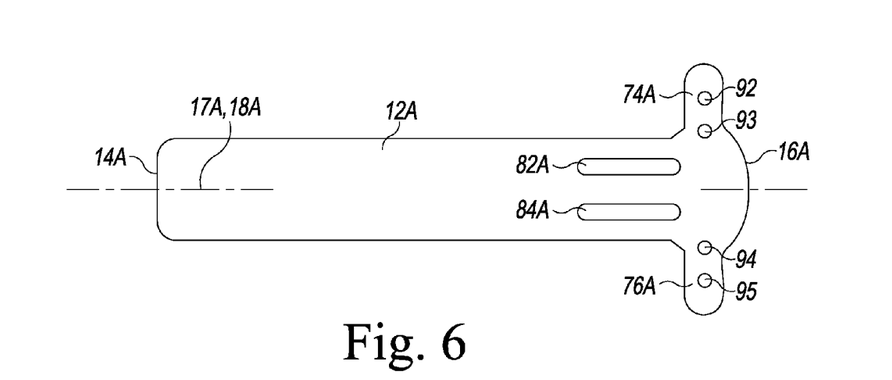
FIG. 6 is a top plan view of an alternative handle.

To allow for proximal-distal movement of the slide member 20, the first illustrated embodiment uses a sliding connection comprising pair of pins and a pair of elongate slots extending in the proximal-distal direction. In FIGS. 1-3, the pins 78, 80 and slots 82, 84 are shown in phantom. As shown in FIGS. 4-5, the pins 78, 80 in the first illustrated embodiment are fixed to and extend upright from the handle 12, and the slots 82, 84 are formed in the slide member 20. It should be understood that the assembly may include structures to prevent the slide member from lifting off of the handle 12. Alternatively, the sliding connection could comprise an elongate dovetail connection.

Figure 7:
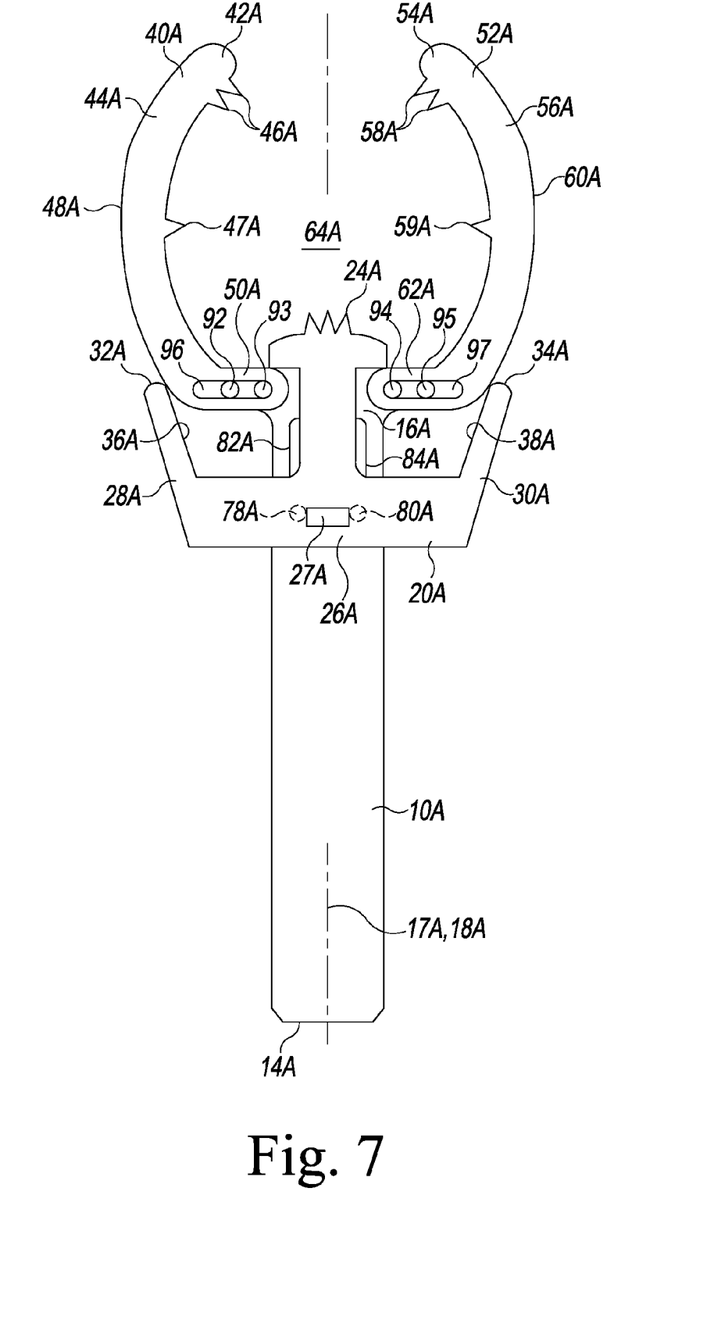
FIG. 7 is a top plan view of a second embodiment of a patella resection assembly embodying the principles of the present invention, utilizing the handle of FIG. 6 and illustrating the patella resection assembly in a first, open position.
Figure 8:
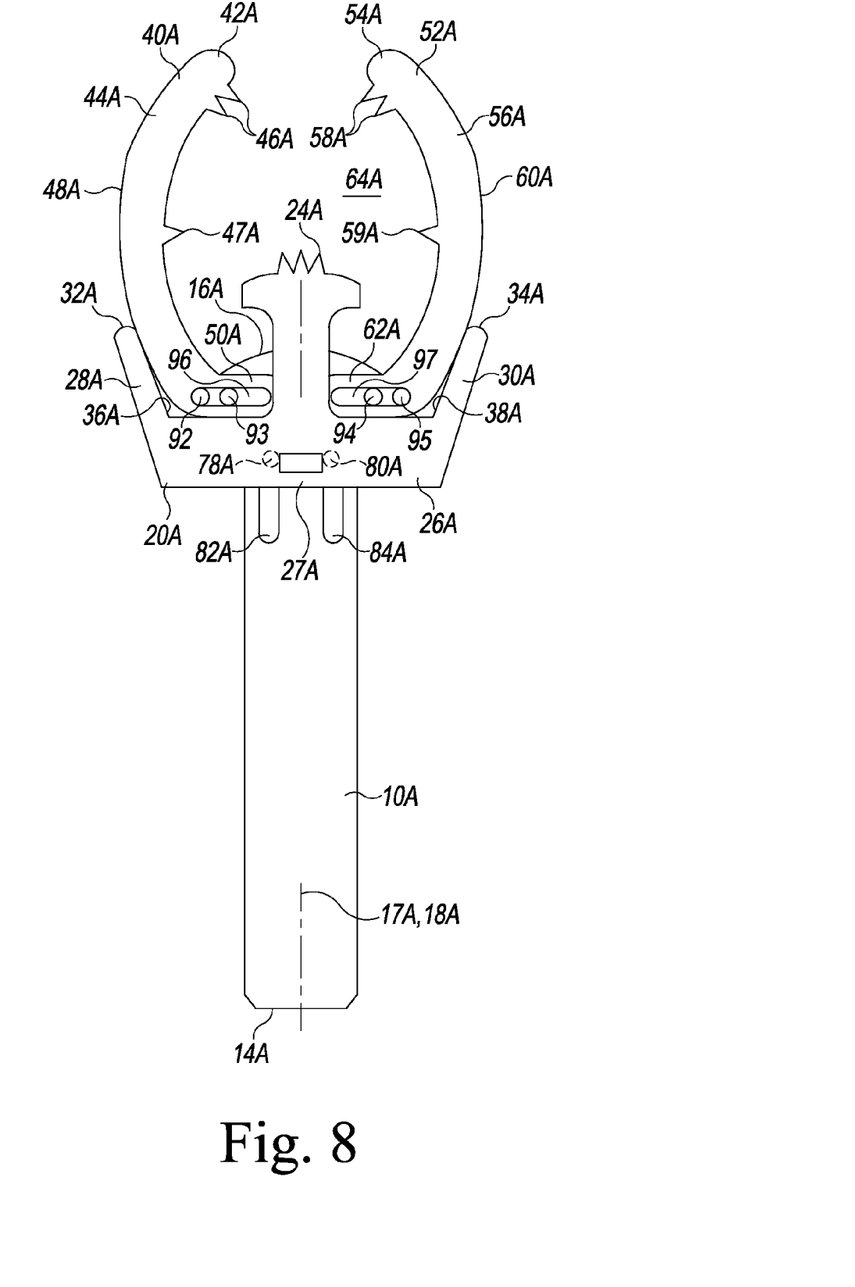
FIG. 8 is a top plan view of the patella resection assembly of FIG. 7, illustrating the patella resection assembly in a second, closed position.

An alternative embodiment of a patella resection assembly is shown in FIGS. 7-8 at 10A. In this embodiment, parts similar to those described above for the first embodiment are shown with reference numbers corresponding to those used for the first embodiment, followed by the letter "A". In the second illustrated embodiment, elongate slots 82A, 84A are formed in the handle 12 instead of the slide member, and pins 78A, 80A extend downward from the slide member 20A to mount the slide member 20A to the handle 12A through a sliding connection. The shoulders 74A, 76A of the handle 12A of the second illustrated patella resection assembly 10A are also shaped differently from the shoulders 74, 76 of the first illustrated patella resection assembly 10. Sliding movement of the slide member 20A is substantially the same as sliding movement of the slide member 20. Structures to prevent the slide member 20A from lifting off of the handle 12A may also be included.

In the second illustrated patella resection assembly 10A, movement of the claw members 40A, 52A from movement of the slide member 20A is linear rather than pivotal. To accomplish this linear movement, the second embodiment provides a linear movement connection comprising pins and slots. In this embodiment, pins 92, 93, 94, 95 extend upwardly from the shoulders or flanges 74A, 76A of the handle 12A and are received in elongate slots 96, 97 in the claw members 40A, 52A. Two pins 92, 93 are linearly aligned and fixed to the shoulder or flange 74A of the handle 12A. Two pins 94, 95 are linearly aligned with each other and with the first two pins 92, 93 and are fixed to the shoulder or flange 76A of the handle 12A. The elongate slots 96, 97 are linearly aligned with each other and are formed in the second ends 50A, 62A of the claw members 40A, 52A. The slots 96, 97 are perpendicular to the longitudinal axis 18A of the handle.

As shown in FIGS. 7-8, as the slide member 20A is moved distally from the position shown in FIG. 7 to the position shown in FIG. 8, the contacts between the diverging inner edges 36A, 38A of the side arms 28A, 30A and curved outer edges 48A, 60A of the claw members 40A, 52A change, so that the contacts are at more proximal portions of the inner edges 36A, 38A of the side arms 28A, 30A and the space between the inner edges 36A, 38A narrows. Thus, distal movement of the slide member 20A forces the claw members 40A, 52A to move towards each other and causes the gap between all of the bone-gripping members 24A, 46A, 58A to decrease until the bone-gripping members contact the periphery of a patella positioned in the opening 64A. In the second illustrated embodiment, distal movement of the slide member 20A pushes the claw members 40A, 52A toward the longitudinal plane 17A to close the opening around the patella.

Additional features may be incorporated into either of the illustrated embodiments. For example, springs or the like may be provided to bias the claw members 40, 40A, 52, 52A to the positions shown in FIGS. 1, 2 and 7. Moreover, additional flat members may be provided overlying and parallel to the surfaces 44, 44A, 56, 56A to define co-planar slots to receive the saw blade used in resecting the patella. The handle 12, 12A and slide member 20, 20A may also include a variety of structures to lock the slide member 20, 20A in preselected positions. For example, a releasable linear ratchet and pawl mechanism could be employed. A stylus could also be assembled with either illustrated patella resection assembly 10, 10A to aid in setting resection level for the patella.

To use the patella resection assembly 10, 10A of the present invention, the surgeon would make a standard incision and then partially or fully evert the patient's patella to expose the posterior side of the patella. With the slide member 20, 20A retracted proximally to the positions shown in FIGS. 1, 2 and 7, the claw members 40, 52, 40A, 52A may be introduced to the surgical site and moved across the patella until the patella is received in the opening 64, 64A. The surgeon may then push on the tab 27, 27A to slide the slide member distally until the bone-gripping members 24, 46, 47, 58, 59, 24A, 46A, 47A, 58A, 59A, contact the periphery of the patella. The surgeon may then continue to push the tab 27, 27A to slide the slide member distally until the bone-gripping members 24, 46, 47, 58, 59, 24A, 46A, 47A, 58A, 59A, fully engage and grip the periphery of the patella. Thus, a variety of sizes of patellae may be clamped through multiple spaced contact points and be held while the co-planar surfaces 44, 56, 44A, 56A (along with the upper surface of the slide member) define the resection level. To resect the patella, the surgeon may place the flat edge of the surgical saw blade along one of the flat, co-planar guide surfaces 44, 56, 44A, 56A and guide the saw blade across the patella until the saw blade rests on an opposite guide surface.

It will be appreciated that the design of the illustrated patella resection assembly 10, 10A allows for selection of the most appropriate and economical material to be used to make the constituent elements. For example, the handle 12 could be made of metal, plastic or other material; the handle 12 may be made relatively inexpensively by injection molding of suitable polymers. The claw members 40, 40A, 52, 52A could also be made of metal, plastic or other material, although it may be preferred to construct the claw member such that at least surfaces 44, 44A and 56, 56A are metal so that appropriate support is provided for the saw blade. In addition, processes such as those described in U.S. Patent Publication No. 2010168753A1, entitled "Orthopaedic Cutting Block Having a Chemically Etched Metal Insert and Method of Manufacturing," the complete disclosure of which is incorporated by reference herein, may be used to make a combination polymer-metal claw member 40, 40A, 52, 52A. Standard metals and polymers for instruments may be used.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

We claim:

1. A patella resection assembly comprising:
   a handle having a proximal end, a distal end, and a longitudinal axis between the proximal end and distal end defining a longitudinal plane;
   a slide member movably mounted on the handle and including a first bone-gripping member, a base, a first arm and a second arm, the first arm and the second arm extending from the base in a distal direction to free distal ends, the first arm being positioned on one side of the longitudinal plane and the second arm being positioned on the opposite side of the longitudinal plane, the first arm having an inner edge facing the longitudinal plane and the second arm having an inner edge facing the longitudinal plane, the inner edges of the first and second arms diverging away from one another in the distal direction;
   the slide member further including a middle arm extending from the base along the longitudinal axis of the handle to a distal end, the first bone-gripping member being at the distal end of the middle arm and including a pointed tooth;
   the slide member being selectively movable in a linear direction along the longitudinal axis of the handle toward and away from the proximal end and distal end of the handle between a first position and a second position, the second position being more distal than the first position;
   a first claw member extending from the distal end of the handle to a first distal free end, the first claw member being positioned on one side of the longitudinal plane, the first claw member having a flat and planar surface for guiding a saw blade, a second bone gripping member at the first distal free end, a curved outer edge and a second end mounted to the handle through a pin and aperture;
   a second claw member extending from the distal end of the handle to a second distal free end, the second claw member being positioned on the other side of the longitudinal plane opposite the position of the first claw member, the second claw member having a flat and planar surface co-planar with the flat and planar surface of the first claw member, a third gripping member at the second distal free end, a curved outer edge and a second end mounted to the handle through a pin and aperture;
   the first distal free end of the first claw member and the second distal free end of the second claw member being spaced distally from the distal end of the handle;
   the first bone-gripping member, first claw member and the second claw member defining an opening between them configured to receive a patella;
   wherein:
   the inner edge of the first arm of the slide member contacts the outer edge of the first claw member and the inner edge of the second arm of the slide member contacts the outer edge of the second claw member;
   longitudinal movement of the slide member from the first position to the second position causes the first bone-gripping member on the middle arm to move distally and the free ends of the first claw member and the second claw member to move toward each other; and
   the opening defined by the first bone-gripping member, first claw member and the second claw member has one size when the slide member is in the first position and a smaller size when the slide member is in the second position.

2. The patella resection assembly of claim 1 further comprising:
   a fourth gripping member extending from the first claw member toward the opening at a position spaced from the free end of the first claw member; and
   a fifth gripping member extending from the second claw member toward the opening at a position spaced from the free end of the second claw member.

3. The patella resection assembly of claim 1 wherein the pins and apertures comprise pivotal connections so that
   longitudinal movement of the slide member from the first position to the second position causes the first claw member and the second claw member to pivot.

4. The patella resection assembly of claim 1 wherein the pins and apertures comprise linear movement connections so that longitudinal movement of the slide member from the first position to the second position causes the first claw member and the second claw member to move linearly toward each other.

5. The patella resection assembly of claim 4 wherein the apertures comprise elongate slots.

* * * * *